United States Patent [19]

Kane et al.

[11] Patent Number: 4,775,689

[45] Date of Patent: Oct. 4, 1988

[54] 5-(NAPHTHYL)-2,4-DIALKYL-3H-1,2,4-TRIAZOLE-3-THIONES AND THEIR USE AS ANTIDEPRESSANTS

[75] Inventors: John M. Kane, Cincinnati; Francis P. Miller, Loveland, both of Ohio

[73] Assignee: Merrell Dow Pharmaceuticals Inc., Cincinnati, Ohio

[21] Appl. No.: 78,500

[22] Filed: Jul. 28, 1987

Related U.S. Application Data

[63] Continuation-in-part of Ser. No. 792,358, Oct. 29, 1985, abandoned.

[51] Int. Cl.$^4$ .................... A61K 31/41; C07D 249/10
[52] U.S. Cl. .................................... 514/384; 514/383
[58] Field of Search ............... 514/383, 384; 548/263, 548/265

[56] References Cited

U.S. PATENT DOCUMENTS 3,514,466  5/1970  Stahle et al. ..................... 548/263
4,414,221  11/1983  Paisons et al. .................... 548/262

OTHER PUBLICATIONS

Daunis et al, Bull. Soc. Chemique de France, (1972), vol. #44, pp. 1511–1520.
Shah et al., J. Pharm. Sci., vol. 58, No. 11, Nov. 1969, pp. 1398–1401.
Heinichart et al, Eur. J. Med. Chem. Clinica Therapeutica, vol. 12, #2, 1977, pp. 117–120.
Guimon et al, Tetrahedron, vol. 31, pp. 2769–2774, (1975).
Yale et al, J. Med. Chem., 9(1), pp. 42–46 (1966).
Mosher et al.
Joshi et al, J. Indean Chem. Ser., vol. 51, Jun. 1974, pp. 613–615.
Maffi et al, Farmaco, vol. 13; 629–38, (1958), Ed. Soc. Chem. Abst. 92:5718z, Egorachten (1979).
Chem. Abst. 69:67340d, Bany (1968).
Chem. Abst. 77:164587, Bany et al. (1972).
Heinichart et al, Molecular Pharmacology, vol. 20, pp. 598–601 (1981).
Sandstrom et al, Aeta Chemica Scandinavica 20, (1966), pp. 57–71, Tautomeric Cyclic Thiones.
Hoggarth, J. Chem. Soc., (1949), pp. 1160–1163.
Kubota et al, Chem. Pharm. Bull., vol. 23, #5 (1975), pp. 955–966, Tautomerism of 3,5 Disubstituted 1,2,4-Triazoles IV.
Derwent Abs. 78045 c/44 J5-5121-5432, 10.9.80.
Kubota et al, Chem. Pharm. Bull., vol. 24, #6 (1976), pp. 1336–1342, 1,2,4-Triazoles VI.

Primary Examiner—Glennon H. Hollrah
Assistant Examiner—D. L. Dinner
Attorney, Agent, or Firm—Edlyn S. Simmons; R. A. McDonald

[57] ABSTRACT

This invention relates to novel 5-(naphthyl)-2,4-dialkyl-3H-1,2,4-triazole-3-thiones and to their use as antidepressants.

15 Claims, No Drawings

5-(NAPHTHYL)-2,4-DIALKYL-3H-1,2,4-TRIAZOLE-3-THIONES AND THEIR USE AS ANTIDEPRESSANTS

This is a continuation-in-part of application Ser. No. 792,358, filed Oct. 29, 1985 now abandoned.

This invention relates to 5-(naphthyl)-2,4-dialkyl-3H-1,2,4-triazole-3-thiones, to their pharmacological properties and to their use as antidepressants.

More specifically, this invention relates to compounds of the formula

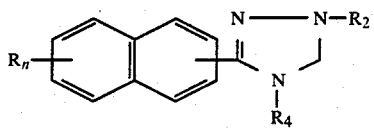

and the tautomers thereof, wherein R represents halogeno, $C_{1-6}$ lower alkyl, $C_{1-6}$ lower alkoxy, hydroxy, or trifluoromethyl with n being zero, 1 or 2, and each of $R_2$ and $R_4$ independently represents $C_{1-6}$ lower alkyl.

For R, halogeno preferably represents chloro or fluoro, and methyl and ethyl represent the preferred lower alkyl moieties, although all the straight and branched manifestations thereof are included. Lower alkoxy radicals include ethers having alkyl moieties of the $C_{1-6}$ alkyl group defined above. Preferably n is one, representing a mono-substituted naphthyl moiety with the R-substituted being a group located at any of the available positions, although positions 5-, 6-, 7- or 8- are preferred for either the mono or di- R-substituted moieties. The tautomeric forms are included for each of the compounds embraced within formula I. Preferably $R_2$ and $R_4$ each represents methyl or ethyl, but may represent any straight or branched alkyl chain.

The compounds of formula I may readily be prepared using processes and procedures analogously known in the art as seen by the following reaction scheme.

Reaction Scheme

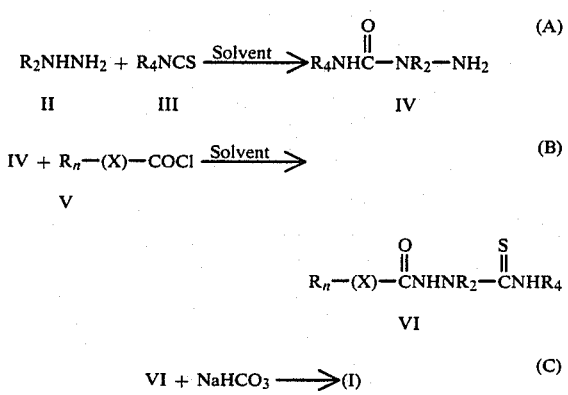

wherein $R_n$, $R_2$ and $R_4$ are as defined above and X represents the optionally substitutted naphthyl moiety of formual I.

In step A, the preparation of the thiosemicarbazides (IV) is readily effected by reacting a $R_2$-substituted hydrazine (II) with a $R_4$-substituted isothiocyanate (III) by contacting the reactants in a suitable solvent. The reaction is quite rapid and may be carried out at 0° C. to room temperature. Although the reaction proceeds rapidly, the mixture may be left for up to 24 hours without significant decrease in yields. Reflux conditions may be employed but are not preferred. Almost all solvents (with the exception of water and organic acids) may be used. Anhydrous alcohols (preferably ethanol or methanol) are preferred although DMF, $CHCl_3$, $CH_2Cl_2$, THF and $Et_2O$ may also be used. The required hydrazines and isothiocyanates are readily available, but may be prepared by known techniques quite obvious to one of ordinary skill in the art.

In Step B, the desired naphthoyl-substituted thiosemicarbazides (VI) may be prepared by reacting the thiosemicarbazides (IV) with an R-substituted-naphthoyl chloride (V) in an aprotic solvent such as pyridine, $CHCl_3$, THF and the like. The acylation proceeds rather easily at temperatures ranging from 0° C. to room temperature over periods of 3 to 24 hours, although elevated temperatures (e.g. reflux temperatures) may be employed. Again, the acid halides (V) generally are commercially available but may also be prepared from the corresponding acids which are available from obvious starting materials.

In Step C, the naphthoyl thiosemicarbazides (VI) are subjected to a cyclization reaction which is effected by heating the compounds (VI) in an aqueous base, e.g. sodium bicarbonate or sodium hydroxide. Alcoholic bases may be utilized, but generally are less desirable. The reaction is conducted at about the reflux temperature of the solvent, preferably at about 65°–100° C. In practice, the thiosemicarbazides (VI) need not be purified for use in Step C.

The following specific examples are given to illustrate the preparation of the compounds of this invention although the scope of compounds exemplified is not meant to be limiting.

Preparation of $R_2$, $R_4$-Substituted-Thiosemicarbazides

EXAMPLE 1

2,4-DIMETHYLTHIOSEMICARBAZIDE

To a stirred solution of methyl hydrazine (16.0 ml, $3.00 \times 10^{-1}$ mole) and sieve dry ethanol (50 ml) was added dropwise a solution of methyl isothiocyanate (22.0 g, $3.00 \times 10^{-1}$ mole) and sieve dry ethanol (30 ml). The reaction was exothermic and gently refluxed as the isothiocyanate was added. A precipitate soon formed. After stirring overnight, the reaction was cooled in an ice bath. The precipitate was then collected by filtration, washed with a little cold isopropanol, and dried by suction, affording a colorless solid: 26.7 g (75%). This material was crystallized two times from water and two times from isopropanol, affording small colorless needles: 14.7 g (41%), mp 135°–137° C.

Preparation of $R_n$ Naphthoyl-$R_2$, $R_4$,-Thiosemicarbazides

EXAMPLE 2

1-(2-NAPHTHOYL)-2,4-DIMETHYLTHIOSEMICARBAZIDE

To a stirred solution of 2,4-dimethylthiosemicarbazide (2.39 g, $2.00 \times 10^{-2}$ mole) and pyridine (20 ml) was added dropwise 2-naphthoyl chloride. (3.89 g, $2.04 \times 10^{31\ 2}$ mole) After stirring at room temperature for 48 hours the reaction was evaporated to dryness, affording a beige solid which was treated with $H_2O$ (100 ml). Filtration of the aqueous mixture gave the desired compound as a beige product, 5.47 g (100%). If pure 1-(2-naphthoyl)-2,4dimethylthiosemicarbazide is desired, the crude product is purified by crystallization.

Preparation of Final Products

EXAMPLE 3

5-(2-NAPHTHYL)-2,4-DIMETHYL-3H-1,2,4-TRIAZOLE-3-THIONE 1-(2-Naphthoyl)-2,4-dimethyl-thiosemicarbazide (5.47 g, $2.00 \times 10^{-2}$ mole) from Example 2 and 1 molar aqueous NaHCO$_3$ (200 ml, $2.00 \times 10^{-1}$ mole) were stirred and warmed to reflux. After refluxing for 17 hours the reaction was allowed to cool to room temperature. The precipitate was collected by filtration, water-washed, and dried by suction. The product was crystallized from isopropyl alcohol to yield off-white, matted needles: 3.9 g (76%) mp. 173°–175° C.

In a similar manner, by substituting the reactants of examples 1–3 with appropriate 2,4-disubstituted thiosemicarbazides and appropriate substituted naphthoyl chlorides, and by substantially following the techniques therein, the following compounds may be readily prepared.

5-(5-fluoro-1-naphthyl)-2,4-dimethyl-3H-1,2,4-triazole-3thione 5-(6-methoxy-2-naphthyl)-2-4-dimethyl-3H-1,2,4-triazole-3thione 5-(7-methyl-2-naphthyl)-2-methyl-4-ethyl-3H-1,2,4 triazole-3-thione 5-(8-chloro-1-naphthyl)-2-ethyl-4-methyl-3H-1,2,4-triazole-3-thione 5-(6,7-dichloro-2-naphthyl)-2,4-diethyl-3H-1,2,4-triazole-3-thione 5-(6,7-difluoro-1-naphthyl)-2,4-dimethyl-3H-1,2,4-triazole-3-thione.

Other compounds embraced within formula I may similarly be prepared by using the procuedures of Examples 1–3.

Using standard laboratory methodology, the pharmacological properties of these compounds and their relative potencies as antidepressants may readily be demonstrated. When compared with other agents clinically known to be useful as antidepressants, the dosage regimen may readily be ascertained by those of ordinary skill in the art.

For example, the assay testing for prevention of reserpine-induced ptosis in mice and in rats is a standard assay. In those test groups, weighed mice or rats are housed individually in wire mesh stick cages and administered test compound or vehicle. At a selected time thereafter, reserpine, prepared as a 4 mg/ml solution in dilute acetic acid, is given to rats at a dose of 4 mg/kg subcutaneously, and to mice as a 0.2 mg/ml solution in dilute acetic acid at a dose of 2 mg/kg intravenously into a tail vein. In each assay the animals are examined individually in a plexiglass cylinder 90 minutes later in the rat assay or 60 minutes after administration of reserpine to mice. Prevention or delay of ptosis is considered significant if the average closure of both eyes is less than 50% after observing for 30 seconds. The ED$_{50}$ for prevention of ptosis is defined as the dose of test compound that significantly prevents ptosis in 50% of the test animals.

Another assay utilized to evaluate antidepressant activity is testing for the antagonism of RO-4-1284*-induced hypothermia. In this test, groups of male mice are weighed and housed individually in wire mesh stick cages. The rectal temperature of each mouse is recorded and the test compound or vehicle is then administered. At a selected time thereafter, RO-4-1284, prepared as a 2 mg/kg solution in distilled water, is administered at a dose of 20 mg/kg i.p. Mice are then placed in a cold room (36° F.) for 30 minutes, and then returned to room temperature for 30 minutes. At this time (60 minutes after RO-4-1284 administration) the rectal temperature of each mouse is again recorded. Under these conditions, RO-4-1284 causes a fall in rectal temperature of more than 6° C. The final temperatures of control groups of ten RO-4-1284-treated mice from a number of experiments are combined to form an "historic control" of 100 mice. This control is updated periodically by replacement of the oldest data. Any drug-treated animal which has final temperature (after RO-4-1284) which is greater than the mean +2 S.D. of the RO-4-1284 historic control is considered to exhibit significant antagonism to the hypothermic effect of RO-4-1284. The ED5% for antagonism is defined as that dose of test compound which significantly antagonizes RO-4-1284 hypothermia in 50% of the test animals. (*Niemegeers, Carlos, J. E. "Antagonism of Reserpine - Like Activity", edited by S. Fielding and H. Lal, published by Futura, pg. 73–98.)

These standard laboratory tests demonstrate that the compounds of this invention have pharmacological effects generally attributed to antidepressants and thus the compounds of this invention will elevate mood in patients suffering from depression and will have an end-use application in the treatment of patients suffering from endogenous depression, a term used interchangeably with psychotic or involutional depression. In this use, the compound (I) will exert a relatively quick onset of action and have a prolonged duration of activity. In general, the compounds may be expected to exert their anti-depressant effects at dose levels of about 0.25–25 mg/kg of body weight per day although, of course, the degree of severity of the disease state, age of the patient and other factors determined by the attending diagnostician will influence the exact course and dosage regimen suitable for each patient. In general the parenterally administered doses are about ¼ to ½ that of the orally administered dose.

For oral administration, the compounds can be formulated into solid or liquid preparations such as capsules, pills, tablets, troches, powders, solutions, suspensions or emulsions. The solid unit dosage forms can be a capsule which can be of the ordinary gelatin type containing, for example, lubricants and inert filler, such as lactose, sucrose or cornstarch. In another embodiment, the compounds of general formula I can be tableted with conventional tablet bases such as lactose, sucrose and cornstarch, in combination with binders, such as acacia, cornstarch or gelatin, disintegrating agents such as potato starch or alginic acid, and a lubricant such as stearic acid or magnesium stearate.

For parenteral administration, the compounds maybe administered as injectable dosages of a solution or suspension of the compound in a physiologically acceptable diluent with a pharmaceutical carrier which can be a sterile liquid such as water, alcohols, oils and other acceptable organic solvents, with or without the addition of a surfactant and other pharmaceutically acceptable adjuvants. Illustrative of oils which can be employed in these preparations are those of petroleum, animal, vegetable, or synthesic origin, for example, peanut oil, soybean oil and mineral oil. In general, water, saline, aqueous dextrose and related sugar solutions, ethanol and glycols such as propylene glycol or polyethylene glycol, or 2-pyrrolidone are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert material such as biodegradable polymers or synthetic silicones, for example Silastic ®, a silicone rubber manufactured by the Dow-Corning Corporation.

As is true in many classes of compounds with a pharmacological activity having a therapeutic end-use application, certain subgeneric groups and certain specific members of the class, because of their overall therapeutic index and their biochemical and pharmacological profile, are preferred. In this instance the preferred compounds are those wherein both $R_2$ and $R_4$ groups are methyl or ethyl, those wherein the R substituent is chloro or fluoro, those wherein $R_n$ substituent is a monochloro or monofluoro substitutent, and those wherein $R_n$ is a dichloro or difluoro substituent.

We claim:

1. A compound of the formula

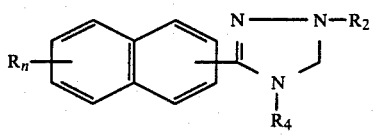

and the tautomers thereof, wherein
R is halogeno, $C_{1-6}$ lower alkyl, $C_{1-6}$ lower alkoxy, hydroxy or trifluoromethyl,
n is zero, 1 or 2, and
$R_2$ and $R_4$ independently represent $C_{1-6}$ lower alkyl.

2. A compound of claim 1 wherein each of $R_2$ and $R_4$ is independently methyl or ethyl.

3. A compound of claim 1 wherein each of $R_2$ and $R_4$ is methyl.

4. A compound of claim 1 wherein R is chloro.

5. A compound of claim 1 wherein R is fluoro.

6. A compound of claim 4 wherein n is one.

7. A compound of claim 5 wherein n is one.

8. A compound of claim 1, said compound being 5-(2-naphthyl)-2,4-dimethyl-3H-1,2,4-triazole-3-thione.

9. A method of treating a patient in need of an antidepressant which comprises administering an effective amount of a compound of the formula

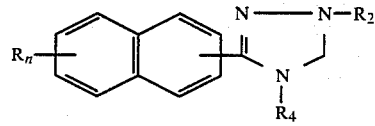

and the tautomers thereof, wherein
R is halogeno, $C_{1-6}$ lower alkyl, $C_{1-6}$ lower alkoxy, hydroxy or trifluoromethyl,
n is zero, 1 or 2, and
$R_2$ and $R_4$ independently represent $C_{1-6}$ lower alkyl.

10. A method according to claim 9 wherein each of $R_2$ and $R_4$ is methyl.

11. A method according to claim 10 wherein R is chloro.

12. A method according to claim 10 wherein R is fluoro.

13. A method according to claim 11 wherein n is one.

14. A method according to claim 12 wherein n is one.

15. A method according to claim 10, said compound being 5(2-naphthyl)-2,4-dimethyl-3H,1,2,4-triazole-3-thione.

* * * * *

UNITED STATES PATENT AND TRADEMARK OFFICE
CERTIFICATE OF CORRECTION

PATENT NO. : 4,775,689

DATED : October 4, 1988

INVENTOR(S) : John M. Kane and Francis P. Miller

It is certified that error appears in the above-identified patent and that said Letters Patent are hereby corrected as shown below:

At Column 1, Line 15 *AND* At Column 5, Line 31 *AND* At Column 6, Line 17 the patent reads:

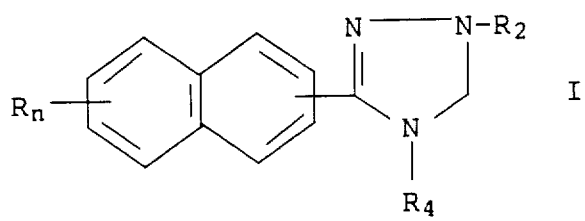

and should read:

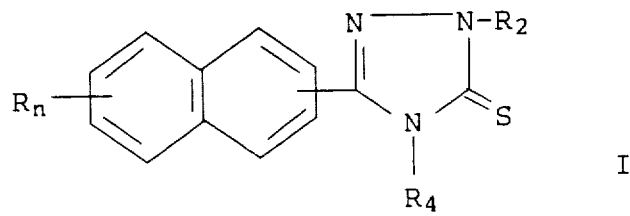

At Column 1, Line 44, the patent reads:

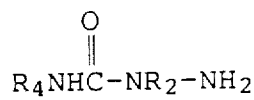

and should read:

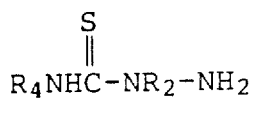

UNITED STATES PATENT AND TRADEMARK OFFICE
CERTIFICATE OF CORRECTION

PATENT NO. : 4,775,689

DATED : October 4, 1988

INVENTOR(S) : John M. Kane and Francis P. Miller

It is certified that error appears in the above-identified patent and that said Letters Patent are hereby corrected as shown below:

At Column 1, Line 61, the patent reads "substitutted" and should read --substituted--.

At Column 1, Line 62, the patent reads "formual" and should read --formula--.

At Column 2, Line 64, the patent reads "X $10^{31}$ 2" and should read --X $10^{-2}$--.

At Column 3, Line 24, the patent reads " 3thione" and should read --3-thione--.

At Column 3, Line 26, the patent reads "3thione" and should read --3-thione--.

At Column 3, Line 27, the patent reads "1,2,4triazole" and should read --1,2,4-triazole--.

At Column 4, Line 18, the patent read reads "ED5%" and should read --$ED_{50}$--.

Signed and Sealed this

Sixth Day of June, 1989

Attest:

DONALD J. QUIGG

Attesting Officer

Commissioner of Patents and Trademarks